US010548839B2

(12) United States Patent
Tian

(10) Patent No.: US 10,548,839 B2
(45) Date of Patent: Feb. 4, 2020

(54) PROCESS OF MANUFACTURING A LYOPHILIZED FAST DISSOLVING, MULTI-PHASIC DOSAGE FORM

(76) Inventor: Wei Tian, Wiltshire (GB)

(*) Notice: Subject to any disclaimer, the term of this patent is extended or adjusted under 35 U.S.C. 154(b) by 0 days.

(21) Appl. No.: 12/724,601

(22) Filed: Mar. 16, 2010

(65) Prior Publication Data

US 2011/0229573 A1    Sep. 22, 2011

(51) Int. Cl.
| | |
|---|---|
| A61K 9/19 | (2006.01) |
| A61K 9/24 | (2006.01) |
| A61K 9/00 | (2006.01) |
| A61K 9/20 | (2006.01) |

(52) U.S. Cl.
CPC .............. *A61K 9/0056* (2013.01); *A61K 9/19* (2013.01); *A61K 9/209* (2013.01); *A61K 9/2018* (2013.01); *A61K 9/2059* (2013.01); *A61K 9/2063* (2013.01)

(58) Field of Classification Search
None
See application file for complete search history.

(56) References Cited

U.S. PATENT DOCUMENTS

| | | | |
|---|---|---|---|
| 5,039,540 A | 8/1991 | Ecanow | |
| 5,044,091 A * | 9/1991 | Ueda | A23L 3/44 34/303 |
| 6,509,040 B1 | 1/2003 | Murray et al. | |
| 6,709,669 B1 | 3/2004 | Murray et al. | |
| 2004/0076666 A1 | 4/2004 | Green et al. | |
| 2006/0008415 A1 * | 1/2006 | Kaisheva | A61K 47/48061 424/1.49 |

FOREIGN PATENT DOCUMENTS

| | | | | |
|---|---|---|---|---|
| CA | 2484724 | | 11/2003 | |
| CA | 2567830 | | 8/2013 | |
| CA | 2793302 | | 4/2017 | |
| CA | 2774210 | | 8/2017 | |
| EP | 1980245 A1 | | 10/2008 | |
| FR | 1373287 A | | 9/1964 | |
| GB | 1548022 A | | 7/1979 | |
| JP | 3-86837 | | 4/1991 | |
| JP | 9-511256 | | 11/1997 | |
| JP | 2001-278779 | | 10/2001 | |
| JP | 2003-529535 | | 10/2003 | |
| WO | 00/50013 A1 | | 8/2000 | |
| WO | 00/61117 A1 | | 10/2000 | |
| WO | WO 2004/043440 | * | 5/2004 | A61K 9/20 |
| WO | 2004/066924 A2 | | 8/2004 | |
| WO | 2006/063189 A2 | | 6/2006 | |
| WO | WO 2008/127669 | * | 10/2008 | A61K 9/24 |

OTHER PUBLICATIONS

International Search Report for corresponding PCT/US2011/028483 dated Mar. 6, 2012.
Seagar, H., "Drug-Delivery Products and Zydis Fast Dissolving Dosage Form," J. Pharm. Pharmaco, vol. 50, pp. 375-382, 1998.
Swarbrick, J., "Gels and Jellies," Encyclopedia of Pharmaceutical Technology, vol. 3, p. 1875, 2007.
Examination Search Report dated Apr. 9, 2015, directed to CA Application No. 2793302; 4 pages.
Examination Search Report dated Jan. 14, 2016, directed to CA Application No. 2793302; 3 pages.
Examination Report dated Oct. 31, 2017, directed to IN Application No. 2342/MUMNP/2012; 5 pages.
Office Action dated Jul. 3, 2018, directed to MX Application No. MX/a/2012/010607; 5 pages.
Office Action dated Nov. 16, 2018, directed to MX Application No. MX/a/2012/010607; 3 pages.
Office Action dated Nov. 6, 2017, directed to MX Application No. MX/a/2012/010607; 5 pages.
Notice of Reasons for Refusal dated Oct. 24, 2014, directed to JP Application No. 2013-500148; 3 pages.
Notification of Defects in Patent Application dated Jun. 15, 2015, directed to IL Application No. 221932; 4 pages.
Office Action dated Aug. 2, 2013, directed to EP Application No. 11712090.7; 4 pages.
Office Action dated Dec. 1, 2017, directed to EP Application No. 11712090.7; 4 pages.
Office Action dated Dec. 16, 2016, directed to EP Application No. 11712090.7; 7 pages.
Office Action dated Dec. 4, 2015, directed to EP Application No. 11712090.7; 6 pages.
The Fourth Office Action dated Feb. 16, 2016, directed to CN Application No. 201180024373.7; 4 pages.
Office Action dated Nov. 20, 2014, directed to KR Application No. 10-2012-7027021; 11 pages.
Patent Examination Report No. 1 dated Oct. 14, 2014, directed to AU Application No. 2011227446; 3 pages.
Patent Examination Report No. 2 dated Apr. 8, 2016, directed to AU Application No. 2011227446; 3 pages.
Pre-Examination Office Action dated Jan. 24, 2019, directed to BR Application No. 112012023324; 5 pages.
The First Office Action dated Mar. 3, 2014, directed to CN Application No. 201180024373.7; 5 pages.
The Second Office Action dated Nov. 25, 2014, directed to CN Application No. 201180024373.7; 5 pages.
The Third Office Action dated Jun. 8, 2015, directed to CN Application No. 201180024373.7; 6 pages.

* cited by examiner

*Primary Examiner* — Kevin S Orwig
(74) *Attorney, Agent, or Firm* — Morrison & Foerster LLP

(57) ABSTRACT

A multi-phasic, lyophilized, fast-dissolving dosage form (FDDF) for the delivery of a pharmaceutically active ingredient is prepared by sequential dosing of a formulation containing a non-gelling matrix forming agent and a formulation containing a gelling gelatin.

11 Claims, No Drawings

PROCESS OF MANUFACTURING A LYOPHILIZED FAST DISSOLVING, MULTI-PHASIC DOSAGE FORM

TECHNICAL FIELD

The instant disclosure relates to a process of manufacturing a lyophilized fast-dissolving dosage form (FDDF) for the delivery of a pharmaceutically active ingredient through sequential dosing of formulations containing matrix forming agents to create a multi-phasic tablet. More specifically, the invention relates to manufacturing a lyophilized FDDF utilizing at least two formulations of matrix forming agents, at least one being a formulation containing a non-gelling matrix forming agent and another being a formulation containing a gelling matrix forming agent, to produce a commercially viable multi-phasic dosage form.

BACKGROUND

A large variety of dosage forms for oral ingestion are known and readily available in the medical field. The most common of these is the tablet. The main limitations of pharmaceutical tablets include poor patient compliance due to difficulty in swallowing and lack of bioavailability of the active through ineffective dissolution of the tablet.

Fast-dissolving dosage forms (FDDFs) are convenient to use and are often used to address issues of patient compliance. There are many forms of FDDFs, for example, "soft" compressed tablets comprising a large amount of wicking/disintegrating agents, tablets comprising a large amount of effervescent agents, and lyophilized tablets. Most commonly, lyophilized, fast dissolving dosage forms, which are designed to release the active ingredient in the oral cavity, are formulated using rapidly soluble gelatin-based matrices. These dosage forms are well known and can be used to deliver a wide range of drugs. Most fast dissolving dosage forms utilize gelatin and mannitol as carriers or matrix forming agents. (Seagar, H., "Drug-Delivery Products and Zydis Fast Dissolving Dosage Form," *J. Pharm. Pharmaco*, vol. 50, p. 375-382 (1998)). Typically, gelatin is used to give sufficient strength to the dosage form to prevent breakage during removal from packaging, but once placed in the mouth, the gelatin allows immediate dissolution of the dosage form. During processing, dosed solution/suspension is preferably frozen by passing through a gaseous medium. This serves to immobilize the solution/suspension rapidly, thereby improving the manufacture efficiency.

Lyophilized dosage forms can be altered by manipulating the amount and type of the structure forming agent in the formulation, most commonly gelatin. However, it has been found that such manipulations tend to upset the delicate balance of viscosity, acceptable dosing temperatures, susceptibility to microbial growth during dosing, and unit disintegration times. These are all critical to obtaining a commercially viable FDDF.

FDDFs manufactured by the freeze drying process such as the Zydis® dosage form are often preferred. They have the distinct advantages of a faster disintegrating time (i.e., less than 5 seconds, as opposed to 1 minute for the loosely compressed tablets), smoother mouth feel (i.e., free of the grittiness associated with the high wicking agents in the compressed tablets), improved pregastric absorption (thereby reduced side effects for certain medications), and increased storage options.

Hydrolyzed mammalian gelatin is often the matrix forming agent of choice in FDDFs because it gels rapidly upon cooling. However, there are problems with using gelling matrix forming agents with the manufacture of biological products or other products where a reduced dosing temperature is desirable to maintain the biological, physical and chemical stability during processing. With products having these characteristics, a matrix forming agent that is not prone to gelling when cooled is selected, such as non-gelling fish gelatin and pullulan, as disclosed in WO 00/61117 and WO 00/50013. However, there are other problems associated with using a non-gelling matrix forming agent. Formulations containing these non-gelling agents typically are not robust and lead to surface deformations when passing through the gaseous cooling medium during freezing. These surface deformations appear as cracks, agglomerates or nodules, and often affect patient compliance. Therefore, there is a need to devise a process that would combine the advantages of both gelling and non-gelling matrix forming agents.

Currently, there is also a need for manufacturing combination pharmaceutical products in FDDFs. In recent years, combination pharmaceutical products have become increasingly popular to treat multiple disease states or the same disease with reduced side effects. Recently launched combination products include: Symbyax® for bipolar depression from Eli Lilly; Lotrel® for hypertension from Novartis; and Caduet® for cardiovascular from Pfizer. However, combination products as FDDFs have been difficult to effectively manufacture, partly because of the typical manufacturing steps of FDDF, i.e., where an aqueous solution/suspension must be prepared and then dosed into preformed blisters before freeze drying. This aqueous solution/suspension must be chemically and morphologically stable throughout the dosing process, which can be problematic for the development of combination products. Therefore, there is a need to manufacture a lyophilized FDDF which controls and effectively eliminates inherent incompatibility of certain active ingredients used in the dosage form.

What is more, an FDDF which controls and effectively eliminates incompatibility between active ingredients and excipients and between multiple excipients during formulation of lyophilized FDDFs would be desirable. For example, preferred flavoring, sweetening, coloring, and buffering systems may be incompatible with active solutions. With regard to excipients, an effervescent couple consisting of citric acid and sodium bicarbonate can not be formulated as an aqueous unitary solution/suspension, but may be preferred in formulating an FDDF system with enhanced drug absorption.

There is also a need for an FDDF that can incorporate multiparticular active pharmaceutical ingredients with or without modified release coating. In particular, a combination of different release profiles, i.e., immediate release and extended release, in one FDDF would be desirable.

U.S. Pat. No. 5,039,540 teaches a method of manufacturing a carrier material having sufficient rigidity for carrying and administering of an active material selected from the group consisting of drugs, nutrients, vitamins, biologically active compounds, foodstuffs, and combinations thereof. This invention has limited applications, as very few pharmaceutically active materials are immiscible in the organic solvent that is used in the pharmaceutical processing. If the active material is even slightly soluble in the organic solvent, the active material would be extracted during the dehydration process, thereby compromising the dose uniformity of the finished products. Further, this reference specifically indicates that the disclosed invention has little similarity to the process of lyophilization.

WO 2004/066924 discloses a pharmaceutical dosage form comprising at least two layers whereby a proton pump inhibitor is in one distinct layer and an aluminum, magnesium or calcium antacid salt is in a second distinct layer. The dosage form can be chewable or rapidly disintegrating. There is no mention of the process of manufacturing a lyophilized FDDF that can disintegrate in the oral cavity. Further, there is no disclosure of manufacture of an FDDF through the sequential dosing of separate solutions/suspensions.

WO 2006/063189 discloses a multi-layered drug delivery system containing at least one gum layer and at least one rapidly dissolving tablet layer. The tablet layer contains a therapeutically effective amount of a medicament which is susceptible to rupture upon chewing, thereby causing release of the drug. There is no disclosure of an FDDF incorporating multiple and sequentially dosed layers.

The present disclosure uses a combination of at least two formulations, one containing a gelling matrix forming agent and the other containing a non-gelling matrix forming agent, which are sequentially dosed in layers to optimize and expand the uses of FDDF to new and potentially previously incompatible agents and to more effective packaging. This is a significant advancement in the state of the art.

SUMMARY OF THE INVENTION

One embodiment of the disclosure is directed to a process of manufacturing a multi-phasic, fast-dissolving dosage form for the delivery of a pharmaceutically active ingredient comprising the sequential steps of: (a) dosing a formulation comprising a non-gelling matrix forming agent into a preformed mold; (b) dosing a formulation comprising a gelling matrix forming agent into the preformed mold; and (c) freeze drying the formulations dosed in steps (a) and (b) to form the multi-phasic, fast-dissolving dosage form.

In certain embodiments of the disclosure, each of the formulations may also contain mannitol and water. In certain embodiments, the non-gelling matrix forming agent is present in an amount ranging from about 1% to about 20% based on weight of the formulation of step (a), the mannitol is present in an amount ranging from about 0% to about 10% based on weight of the formulation of step (a), and/or water is present in an amount ranging from about 50% to about 98% based on weight of the formulation of step (a). In certain embodiments, the gelling matrix forming agent is present in an amount ranging from about 0.2% to about 15% based on weight of the formulation of step (b), the mannitol is present in an amount ranging from about 1% to about 10% based on weight of the formulation of step (b), and/or water is present in an amount ranging from about 50% to about 98% based on weight of the formulation of step (b).

In certain embodiments of the disclosure, step (a) is conducted at a temperature ranging from about 1° C. to about 30° C. and/or step (b) is conducted at a temperature ranging from about 15° C. to about 30° C.

The method of the present disclosure includes several optional sub-steps and steps such as freezing the formulations of steps (a) and (b) prior to step (c) and repeating one or both of steps (a) and (b) at least once.

The present disclosure is also directed to a multi-phasic, fast-dissolving dosage form made according to the process of the present invention.

The present disclosure is also directed to a multi-phasic, lyophilized, fast-dissolving dosage form for the delivery of a pharmaceutically active ingredient comprising: (a) at least one gelled matrix layer; and (b) at least one non-gelled matrix layer. In certain preferred embodiments, the weight ratio of gelled matrix layer to non-gelled matrix layer is from about 1:5 to about 5:1.

The present disclosure attempts to solve the foregoing problems in the art, namely to develop an FDDF that is manufactured successfully and efficiently, and that, through its multi-phasic form, allows for: the manufacture of combination products, including combinations of previously incompatible excipients and/or active ingredients to be delivered in the same dosage form and combinations of formulations with different release profiles.

DETAILED DESCRIPTION OF THE INVENTION

The first embodiment is directed to a process of manufacturing a multi-phasic, fast-dissolving dosage form for the delivery of a pharmaceutically active ingredient comprising the sequential steps of: (a) dosing a formulation comprising a non-gelling matrix forming agent into a preformed mold; (b) dosing a formulation comprising a gelling matrix forming agent into the preformed mold; and (c) freeze drying the formulations dosed in steps (a) and (b) to form the multi-phasic, fast-dissolving dosage form. In other words, two or more unitary formulations are provided and dosed sequentially prior to freeze-drying. "Sequentially dosed" or "dosed sequentially" as used herein refers to a process of dosing one formulation comprising at least one matrix forming agent followed by dosing another formulation comprising at least one matrix forming agent, such that the two formulations are not dosed at the same time, and may be dosed under different conditions, such as at different temperatures.

In the first step of the present method, a formulation comprising a non-gelling matrix forming agent is dosed into a preformed mold. As used herein, "non-gelling matrix forming agent" refers to a polymer having a ratio of viscosity at 5° C. over viscosity at 25° C. of 4 or less. Viscosity may be determined by a Haake™ viscometer or other conventional viscometer using concentric cylinders or other configurations. Whether a polymer is a gelling or non-gelling matrix forming agent depends not only on the chemical nature, but also on concentration and other formulation components. In fact, depending on molecular modification (e.g., depolymerization through hydrolysis, or derivatization of the side chain groups), concentration, as well as the absence of other molecules that may induce gelation (e.g., potassium ion for carageenan, calcium ion for alginate), almost all gelling polymers can be transformed into non-gelling polymers where gelation does not occur and the polymers function as thickener in the formulation.

As used herein, "dosed" refers to the deposition of a pre-determined aliquot of solution or suspension. As used herein, "preformed mold" refers to any suitable container or compartment into which an aqueous solution or suspension may be deposited and within which subsequently freeze dried; in certain preferred embodiments of the present disclosure, the preformed mold is a blister pack with one or more blister pockets. The formulation of step (a), upon further processing, i.e., freeze drying, forms the first layer of the multi-phasic, fast-dissolving dosage form of the present invention.

Any conventional non-gelling matrix forming agent may be used for purposes of the present invention. Suitable non-gelling matrix forming agents include, without limitation, non-gelling gelatins, modified starches, pullulan, non-gelling fish gelatin, maltodextrins, low molecular weight dextrans, starch ethers, low to intermediate molecular weight cellulose gums, and combinations thereof. The amount of non-gelling matrix forming agent present in the formulation of step (a) ranges preferably from about 1% to about 20%, more preferably from about 2% to about 15%, and most preferably from about 4% to about 10% based on weight of the formulation of step (a).

The formulation of step (a) is typically in the form of a solution or suspension. Accordingly, a solvent is also present in the formulation. A suitable solvent can be readily chosen by one of ordinary skill in the art once the final composition of the formulation is known, i.e., pharmaceutically active ingredient, excipient, etc. to be present. Preferred solvents include ethanol, isopropanol, other lower alkanols and water, and, more preferably, water. The amount of solvent, preferably water, present in the formulation of step (a) ranges preferably from about 50% to about 98%, more preferably from about 65% to about 98%, and most preferably from about 75% to about 95% based on weight of the formulation of step (a).

The formulation of step (a) may also contain an additional pharmaceutically acceptable agent or excipient. Such additional pharmaceutically acceptable agents or excipients include, without limitation, sugars, such as mannitol, dextrose, and lactose, inorganic salts, such as sodium chloride and aluminum silicates, gelatins of mammalian origin, fish gelatin, modified starches, preservatives, antioxidants, surfactants, viscosity enhancers, coloring agents, flavoring agents, pH modifiers, sweeteners, taste-masking agents, and combinations thereof. Suitable coloring agents include red, black and yellow iron oxides and FD & C dyes such as FD & C Blue No. 2 and FD & C Red No. 40, and combinations thereof. Suitable flavoring agents include mint, raspberry, licorice, orange, lemon, grapefruit, caramel, vanilla, cherry and grape flavors and combinations of these. Suitable pH modifiers include citric acid, tartaric acid, phosphoric acid, hydrochloric acid, maleic acid and sodium hydroxide, and combinations thereof. Suitable sweeteners include aspartame, acesulfame K and thaumatin, and combinations thereof. Suitable taste-masking agents include sodium bicarbonate, ion-exchange resins, cyclodextrin inclusion compounds, adsorbates or microencapsulated actives, and combinations thereof. One of ordinary skill in the art can readily determine suitable amounts of these various additional excipients if desired. Mannitol, which is an organic compound with the formula $(C_6H_8(OH)_6)$ and is known generally to those in the art, is a preferred additional pharmaceutically acceptable agent. When present, an additional pharmaceutically acceptable agent, preferably mannitol, is present in the formulation of step (a) in an amount ranging preferably from about 0% to about 10%, more preferably from about 2% to about 8%, and most preferably from about 3% to about 6% based on weight of the formulation of step (a).

The formulation of step (a) may also contain a pharmaceutically active ingredient. As used herein, "pharmaceutically active ingredient" refers to a drug product that may be used in the diagnosis, cure, mitigation, treatment or prevention of disease. Any pharmaceutically active ingredient may be used for purposes of the present invention. Of course, one of ordinary skill in the art will readily understand that certain pharmaceutically active ingredients are more suitable for use with the non-gelling matrix forming agent of the formulation of step (a) than with, for example, the gelling matrix forming agent of step (b). Suitable pharmaceutically active ingredients include, without limitation: analgesics and anti-inflammatory agents, antacids, anthelmintics, anti-arrhythmic agents, anti-bacterial agents, anti-coagulants, anti-depressants, anti-diabetics, anti-diarrheals, anti-epileptics, anti-fungal agents, anti-gout agents, anti-hypertensive agents, anti-malarials, anti-migraine agents, anti-muscarinic agents, anti-neoplastic agents and immunosuppressants, anti-protazoal agents, anti-rheumatics, anti-thyroid agents, antivirals, anxiolytics, sedatives, hypnotics and neuroleptics, beta-blockers, cardiac inotropic agents, corticosteroids, cough suppressants, cytotoxics, decongestants, diuretics, enzymes, anti-parkinsonian agents, gastro-intestinal agents, histamine receptor antagonists, lipid regulating agents, local anesthetics, neuromuscular agents, nitrates and anti-anginal agents, nutritional agents, opioid analgesics, oral vaccines, proteins, peptides and recombinant drugs, sex hormones and contraceptives, spermicides, and stimulants; and combinations thereof. A list of specific examples of these active ingredients may be found in U.S. Pat. No. 6,709,669, which is incorporated herein by reference. When present, the pharmaceutically active ingredient is present in the formulation of step (a) in an amount that is necessary to exhibit the required physiological effect as established by clinical studies. One of ordinary skill in the art can readily determine an appropriate amount of active ingredient to include in the multi-phasic dosage form made according to the present disclosure.

The formulation of step (a) can be made by any conventional method. Most typically, the non-gelling matrix forming agent, solvent and optional ingredients may be mixed together at any temperature, though preferably between about 40° C. to about 80° C., to form a solution. The solution may then be cooled to a subambient temperature, preferably from about 1° C. to about 30° C., more preferably from about 2° C. to about 20° C., and most preferably from about 5° C. to about 15° C., at which point the active ingredient may be added.

Likewise the dosing of step (a) can be accomplished by any known method or apparatus. Dosing is preferably performed at subambient temperatures, preferably from about 2° C. to about 20° C., and more preferably from about 5° C. to about 15° C.

In a preferred embodiment, the formulation of step (a) comprises a non-gelling matrix forming agent, mannitol and water, and in some embodiments, an additional pharmaceutically acceptable excipient. Preferably, this formulation comprises from about 1% to about 20% non-gelling matrix forming agent, about 0% to about 10% mannitol, about 50% to about 98% water, and about 0% to about 50% of an excipient, more preferably about 2% to about 15% non-gelling matrix forming agent, about 2% to about 8% mannitol, about 65% to about 98% water, about 0% to about 20% of an excipient, and most preferably about 4% to about 10% non-gelling matrix forming agent, about 3% to about 6% mannitol, about 75% to about 95% water and about 0% to about 10% of an excipient.

According to certain embodiments of the disclosure, step (a) is repeated one or more times prior to performing step (b). In this way, additional layers of the multi-phasic, fast-dissolving dosage form of the present invention may be formed. There is no limit to the number of layers that may be formed using step (a); however, step (b) must follow the performance of one or more step (a), such that the final layer contains a gelling matrix forming agent.

In the second step of the present method, a formulation comprising a gelling matrix forming agent is dosed into the preformed mold. As used herein, "gelling matrix forming agent" refers to a polymer formulation that has a ratio of bulk viscosity at 5° C. over the bulk viscosity at 25° C. of at least 5, and more preferably, a ratio of 7.5 or over. Gelling polymers are polymers that can form cross links that underpin the network structure. They are extensively discussed in "Gels and Jellies," by James Swarbrick, *Encyclopedia of Pharmaceutical Technology*, Vol. 3, p. 1875 (2007). Since step (b) is performed after step (a), the formulation containing the gelling matrix forming agent is deposited or dosed on top of the formulation containing the non-gelling matrix forming agent. The formulation of step (b), upon subsequent processing, i.e., freeze-drying, forms another layer of the multi-phasic, fast-dissolving dosage form of the present invention.

Any conventional gelling matrix forming agent may be used for purposes of the present disclosure. Suitable gelling matrix forming agents include, without limitation, gelling gelatin, carageenan gums, hyaluronic acid, pectins, starches, carboxymethyl cellulose sodium, agar, gellan gum, guar gum, tragacanthan gum, hydroxypropyl cellulose, hydroxy propyl methylcellulose, methylcellulose, carbomer, poloxamer, polyacrylic acid, polyvinyl alcohol, alginates and poly(glycolic acid), and combinations thereof. The amount of gelling matrix forming agent present in the formulation of step (a) ranges preferably from about 0.2% to about 15%, more preferably from about 0.5% to about 10%, and most preferably from about 1% to about 4% based on weight of the formulation of step (b).

The formulation of step (b) is typically in the form of a solution or suspension. Accordingly, a solvent is also present in the formulation. A suitable solvent can be readily chosen by one of ordinary skill in the art once the final composition of the formulation is known, i.e., pharmaceutically active ingredient, excipient, etc. to be present. Preferred solvents include ethanol, isopropanol and water, and more preferably, water. The amount of solvent present in the formulation of step (b) ranges preferably from about 50% to about 98%, more preferably from about 65% to about 98%, and most preferably from about 75% to about 95% based on weight of the formulation of step (b).

The formulation of step (b) may also contain an additional pharmaceutically acceptable agent or excipient, defined as above. When present, an additional pharmaceutically acceptable agent, preferably mannitol, is present in the formulation of step (b) in an amount ranging preferably from about 1% to about 10%, more preferably from about 2% to about 8%, and most preferably from about 3% to about 6% based on weight of the formulation of step (b).

The formulation of step (b) may also contain a pharmaceutically active ingredient, defined as above. When present, the pharmaceutically active ingredient is present in the formulation of step (b) in an amount that is necessary to exhibit the required physiological effect as established by clinical studies. One of ordinary skill in the art can readily determine an appropriate amount of active ingredient to include in the multi-phasic dosage form made according to the present disclosure.

The formulation of step (b) can be made by any conventional method. Most typically, the gelling matrix forming agent, solvent and optional ingredients may be mixed together at any temperature, though preferably between about 40° C. to about 80° C., to form a solution. The solution may then be cooled to ambient temperature, preferably from about 15° C. to about 30° C., and more preferably from about 20° C. to about 30° C., at which point the active ingredient may be added.

Likewise the dosing of step (b) can be accomplished by any known method or apparatus. The dosing is preferably performed at the same temperature to which the formulation is cooled after preparation, i.e., preferably about 20° C. to about 30° C.

In a preferred embodiment, the formulation of step (b) comprises a gelling gelatin, mannitol and water, and in some embodiments, an additional pharmaceutically acceptable excipient. More preferably, this formulation comprises from about 0.2% to about 15% gelling gelatin, about 1% to about 10% mannitol, about 50% to about 98% water, and about 0% to about 50% of an excipient, still more preferably about 0.5% to about 10% gelling gelatin, about 2% to about 8% mannitol, about 65% to about 98% water, about 0% to about 20% of an excipient, and most preferably about 1% to about 4% gelling gelatin, about 3% to about 6% mannitol, about 75% to about 95% water and about 0% to about 10% of an excipient.

According to certain embodiments of the invention, step (b) is repeated one or more times prior to performing step (c). In this way, additional layers of the multi-phasic, fast-dissolving dosage form of the present invention may be formed. Step (b) may be repeated one or more times regardless of whether step (a) is also repeated. Preferably, it is not repeated more than four times without also repeating step (a).

In the third step of the present invention, the formulations dosed in steps (a) and (b) are freeze dried to form the multi-phasic, fast-dissolving dosage form. In a preferred embodiment, step (c) comprises the sub-steps of (c1) freezing the forms dosed in steps (a) and (b) and then (c2) freeze drying the formulations dosed in steps (a) and (b) to form the multi-phasic, fast-dissolving dosage form of the present invention. Typically, the dosed formulations in the preformed molds are frozen by any means known in the art, for example by passing them through a liquid nitrogen tunnel, preferably for about one to about ten minutes. One of ordinary skill in the art would readily understand the speed with which to pass them through the tunnel. The dosed formulations in the preformed molds are then freeze dried under vacuum.

A second embodiment of the disclosure is directed to a multi-phasic, fast-dissolving dosage form made according to the process of the first embodiment of the disclosure. And a third embodiment of the disclosure is directed to a multi-phasic, lyophilized, fast-dissolving dosage form for the delivery of a pharmaceutically active ingredient comprising: (a) at least one gelled matrix layer; and (b) at least one non-gelled matrix layer.

As used herein, the term "non-gelled matrix layer" refers to a layer formed within a preformed mold, said layer comprising a non-gelling matrix forming agent, and, optionally, solvents, pharmaceutically active ingredients, excipients and/or other matrix forming agents, which has preferably been sequentially dosed into the preformed molds, frozen and freeze-dried as explained above with regard to the first embodiment of the disclosure. In a preferred embodiment, the non-gelled matrix layer is comprised of a formulation comprising a non-gelling matrix forming agent, mannitol and water.

Also as used herein, the term "gelled matrix layer" refers to a layer formed within a preformed mold, said layer comprising a gelling matrix forming agent, and, optionally, solvents, pharmaceutically active ingredients, excipients and/or additional pharmaceutically acceptable agents, which has preferably been sequentially dosed into the preformed molds, frozen and freeze-dried as explained above with regard to the first embodiment of the disclosure. In a preferred embodiment, the gelled matrix layer is comprised of a formulation comprising a gelling gelatin, mannitol and water.

The details noted above regarding the identification of pharmaceutically active ingredients, gelling matrix forming agents, non-gelling matrix forming agents, preformed molds, additional pharmaceutically acceptable agents, excipients, ingredients, etc. are the same for the second and third embodiments of the disclosure as for the first embodiment of the disclosure.

In the multi-phasic, lyophilized, fast-dissolving dosage forms of the second and third embodiments of the disclosure, the weight ratio of gelled matrix layer to non-gelled matrix layer preferably ranges from about 1:5 to about 5:1, more preferably ranges from about 1:4 to about 4:1, and is most preferably about 1:2 to about 2:1.

The dosage forms of the present invention are fast-dissolving dosage forms and accordingly have the distinct advantage of a faster disintegrating time. The route of administration may be oral, vaginal or nasal, though preferably oral. Once placed in the oral cavity and in contact with saliva, a dosage form can disintegrate within about 1 to about 60 seconds, preferably within about 1 to about 30 seconds, more preferably within about 1 to about 10 seconds and most preferably in less than about 5 seconds. The dosage forms of the present invention are similar to the dosage forms described in U.K. Pat. No. 1548022, that is, solid fast dissolving dosage forms comprising a network of the active ingredient and a water-soluble or water-dispersible carrier, which is inert toward the active ingredient, the network having been obtained by subliming solvent from a composition in the solid state, that composition comprising the active ingredient and a solution of the carrier in a solvent. However, the '022 patent provides no guidance or suggestion with regard to the formulation of multi-phasic forms.

In fact, the multi-phasic dosage form of the present invention is an excellent delivery system since it is comprised of at least two distinct layers. Therefore, it is possible to use two incompatible active ingredients or excipients, since one may be placed in one layer and the other placed in another layer. Furthermore, it is possible to take advantage of using a gelling gelatin as the matrix forming agent, i.e., minimal surface deformations on manufactured tablets, and to take advantage of using a non-gelling matrix forming agent, i.e. effective with biological products. In other words, the advantages of both gelling and non-gelling matrix forming agents in a lyophilization formulation can be attained.

EXAMPLES

The present invention is not limited to any specific drug, but to solving the problems of certain drugs when formulated into an FDDF. The following examples will illustrate the practice of the present invention in some of the preferred embodiments. Other embodiments within the scope of the claims will be apparent to one skilled in the art.

Example 1

A lyophilized FDDF of the kind known in the art as described in Seagar, H., "Drug-Delivery Products and Zydis Fast Dissolving Dosage Form," *J. Pharm. Pharmaco*, vol. 50, p. 375-382 (1998) was prepared, but with two formulations containing matrix forming agents. Formulation 1a (non-gelling) and Formulation 1b (gelling) were prepared having the compositions set forth in Table 1 below. First, Formulation 1a was prepared by combining the modified starch, mannitol and water and heating the mixture to 75° C. for 15 minutes. The solution was subsequently cooled to 5° C. in a chilled water bath and kept at 5° C. while Formulation 1a was dosed into 400 blister pockets using a semi-automatic Hamilton dosing pump dispensing 150 mg per dose. Formulation 1b was prepared by combining the gelatin, mannitol and water and heating the mixture to 60° C. for 15 minutes. The solution was subsequently cooled to ambient temperature, e.g., 20-25° C., in a chilled water bath and kept at ambient temperatures while it was dosed in a layer over Formulation 1a in the 400 blister pockets, thus forming two layers. The dosed formulations were then rapidly frozen by being passed through a liquid nitrogen freeze tunnel having a preset temperature of −80° C. for 3.25 minutes. The frozen units were subsequently freeze dried in a Usiforid SMH90 freeze drier with a shelf temperature of 0° C. and a chamber pressure of 0.5 mbar for 6 hours. The freeze dried tablets were visually inspected; no major defects were found. The tablets disintegrated instantly, within two seconds, on being placed in purified water at 37° C., measured by the modified USP disintegration method.

Comparative Example 1

The temperature was set to 5° C. and 300 mg of Formulation 1a was dosed into the blister pockets and processed under the same conditions as Example 1, i.e., freezing, freeze-drying. The freeze dried tablets were inspected in the same manner as in Example 1. Significant surface agglomerates (>2 mm) were found on 75% of the tablets.

Example 2

A multi-phasic, lyophilized FDDF was prepared using Formulation 2a (non-gelling) and Formulation 2b (gelling) having the compositions set forth in Table 1 below. A total of 150 mg of Formulation 2a was prepared by combining the modified starch, mannitol and water and heating the mixture to 60° C. for 15 minutes. The solution was subsequently cooled to 5° C. in a chilled water bath and kept at 5° C. while Formulation 2a was dosed into 400 blister pockets using a semi-automatic Hamilton dosing pump dispensing 150 mg per dose. Formulation 2b was prepared by combining the gelatin, mannitol and water and heating the mixture to 60° C. for 15 minutes. The solution was subsequently cooled to ambient temperature, e.g., 20-30° C., in a chilled water bath and kept at ambient temperature while it was dosed in a layer over Formulation 2a in the 400 blister pockets, thus forming two layers. The blister pockets were subsequently treated in the same manner as in Example 1.

The freeze dried tablets were inspected for surface defects; no major defects were found on the FDDFs prepared. The disintegration time was less than 2 seconds for the FDDFs as measured by the modified USP disintegration method.

Another multi-phasic, lyophilized FDDF was prepared with a total of 150 mg of Formulation 2a, which was prepared and cooled to 5° C. in a chilled water bath and kept at 5° C. while it was dosed into 400 blister pockets. Formulation 2c (see Table 1 below) was prepared by combining the gelatin, mannitol and water and heating the mixture to 60° C. for 15 minutes. The solution was subsequently cooled to ambient temperature, e.g., 20-30° C., in a chilled water bath and kept at ambient temperatures while it was dosed in a layer over Formulation 2a. The blister pockets were subsequently treated in the same manner as in Example 1.

The freeze dried tablets were inspected for surface defects; no major defects were found on the FDDFs prepared. The disintegration time was less than 2 seconds for the FDDFs as measured by the modified USP disintegration method Comparative Example 2

A multi-phasic, lyophilized FDDF was prepared with a total of 150 mg of Formulation 2a (non-gelling), which was dosed into 380 blister pockets at 5° C. Subsequently, a total of 150 mg of Formulation 2d (non-gelling), prepared in the same manner as Formulation 2c, was dosed in a layer over Formulation 2a at ambient temperature. The compositions of Formulations 2a and 2d are set forth in Table 1 below. The freeze dried tablets were inspected and surface agglomerates were found on 5% of the tablets. The tablets had a disintegration time of less than 1 second as determined by the modified USP disintegration testing method.

Example 3

A multi-phasic, lyophilized FDDF of the present invention was then tested for industrial applicability. The compositions of Formulations 3a and 3b are set forth in Table 1 below. The tablets were prepared using a total of 50 kg of Formulation 3a, which was prepared by combining the gelatin, mannitol and water and heating the mixture using a 60 litres Becomix™ mixer to 60° C. for 60 minutes. The solution was subsequently cooled to 10° C. in a chilled water bath and kept at 10° C. while Formulation 3a was dosed into 33,600 blister pockets, immediately followed by dosing a total of 50 kg of Formulation 3b, which was prepared in the same manner as Formulation 3a but cooled to 23° C., ambient temperature, over Formulation 3a at ambient temperature. The blister pockets were subsequently treated in the same manner as in Example 1. The freeze dried tablets were inspected for surface defects and 99.98% were free of any defects, including cracking, agglomerates on top of the units and protruded frost heaves.

TABLE 1

FORMULATIONS

| Formulation | Gelling Gelatin | Non-Gelling Matrix Forming Agent | Mannitol | H₂O | NaOH | Sodium Bicarbonate | Citric Acid |
|---|---|---|---|---|---|---|---|
| 1a | | modified starch 6.5 | 3.5 | 90 | | | |
| 1b | 4 | | 3.5 | 92.5 | | | |
| 2a | | sourced from Norland 6.75 | 5.08 | 87.53 | 0.64 | | |
| 2b | Sourced from Gelita 4 | | 3 | 92.84 | 0.16 | | |
| 2c | | Sourced from Lappi 3 | 5.08 | 91.80 | 0.12 | | |
| 2d | | Sourced from Norland | 5.08 | 91.82 | 0.10 | | |
| 3a | | 3.0 Sourced from Norland 5.5 | 5 | 89.5 | | | |
| 3b | Sourced from Gelita 4 | | 3.0 | 93.0 | | | |

Thus, there are numerous advantages to the sequential dosing of a formulation comprising non-gelling matrix forming agent and a formulation containing gelling gelatin for manufacture of lyophilized FDDFs. The resulting multi-phasic, lyophilized FDDF makes possible certain uses of the dosage form, which are not known or suggested in the prior art.

Numerous alterations, modifications, and variations of the preferred embodiments disclosed herein will be apparent to those skilled in the art and they are all anticipated and contemplated to be within the spirit and scope of the claimed invention. For example, although specific embodiments have been described in detail, those with skill in the art will understand that the preceding embodiments and variations can be modified to incorporate various types of substitute, additional or alternative materials. Accordingly, even though only few variations of the present invention are described herein, it is to be understood that the practice of such additional modifications and variations and the equivalents thereof, are within the spirit and scope of the invention as defined in the following claims. All patent applications, patents, and other publications cited herein are incorporated by reference in their entirety.

What is claimed is:

1. A process of manufacturing a multi-phasic, fast-dissolving dosage form for the delivery of a pharmaceutically active ingredient comprising, in the following order, the steps of:
   (a) cooling a formulation comprising 4-10 wt. % non-gelling matrix forming agent, 3-6 wt. % mannitol, and water to a temperature ranging from 2° C. to 15° C. and while maintaining the temperature from 2° C. to 15° C., dosing the formulation comprising the non-gelling matrix forming agent into a preformed mold, wherein the non-gelling matrix forming agent is selected from the group consisting of non-gelling gelatins, modified starches, and combinations thereof;
   (b) cooling a formulation comprising 1-4 wt. % gelling matrix forming agent, 3-6 wt. % mannitol, and water to a temperature from 20° C. to 30° C. and while maintaining the temperature from 20° C. to 30° C., dosing the formulation comprising the gelling matrix forming agent into the preformed mold of step (a); and
   (c) freeze drying the formulations dosed in steps (a) and (b) to form the multi-phasic, fast-dissolving dosage form;
   wherein step (c) comprises the sub-steps of (c1) freezing the formulations dosed in steps (a) and (b) within the preformed mold; and (c2) freeze drying the formulations dosed in steps (a) and (b), wherein the formulation dosed in step (a) forms a first layer of the dosage form, wherein the formulation dosed in step (b) forms a second layer of the dosage form distinct from the first layer, and wherein the first layer and the second layer of the dosage form disintegrate within 1 to 30 seconds.

2. The process according to claim 1, wherein the at least one non-gelling gelatin is pullulan.

3. The process according to claim 1, wherein the water is present in an amount ranging from about 50% to about 98% based on weight of the formulation of step (a).

4. The process according to claim 1, wherein the gelling matrix forming agent is selected from the group consisting of gelling gelatins, gelling polymers having a ratio of bulk viscosity at 5° C. over bulk viscosity at 25° C. of at least 5, and combinations thereof.

5. The process according to claim 1, wherein the water is present in an amount ranging from about 50% to about 98% based on weight of the formulation of step (b).

6. The process according to claim 1 further comprising repeating step (a) at least once prior to step (b).

7. The process according to claim 1 further comprising repeating step (b) at least once prior to step (c).

8. A process of manufacturing a multi-phasic, fast-dissolving dosage form for the delivery of a pharmaceutically active ingredient comprising, in the following order, the steps of:

(a) dosing a formulation comprising 4-10 wt. % non-gelling matrix forming agent, 3-6 wt. % mannitol, and water into a preformed mold, wherein the non-gelling matrix forming agent is selected from the group consisting of non-gelling gelatins, modified starches, and combinations thereof, and wherein the formulation dosed in step (a) forms a first layer of the fast-dissolving dosage form upon completion of step (c) below;

(b) subsequent to step (a), dosing a formulation comprising 1-4 wt. % gelling matrix forming agent, 3-6 wt. % mannitol, and water into the preformed mold, wherein the formulation dosed in step (b) forms a second layer of the fast-dissolving dosage form upon completion of step (c) below;

(c) freeze-drying the formulations dosed in steps (a) and (b) to form the multi-phasic, fast-dissolving dosage form, wherein the first layer and the second layer of the dosage form disintegrate within 1 to 30 seconds.

9. The process according to claim 8, wherein the formulation dosed in step (a) is a solution or a suspension.

10. The process according to claim 8, wherein the formulation dosed in step (b) is a solution or a suspension.

11. The process according to claim 8, wherein the gelling matrix forming agent is selected from the group consisting of gelling gelatins, gelling polymers having a ratio of bulk viscosity at 5° C. over bulk viscosity at 25° C. of at least 5, and combinations thereof.

\* \* \* \* \*